(12) United States Patent
Rivard

(10) Patent No.: US 10,682,262 B2
(45) Date of Patent: Jun. 16, 2020

(54) LIMB-MOUNTED NOSE WIPING DEVICE

(71) Applicant: Catherine L. Rivard, Edgewood, NM (US)

(72) Inventor: Catherine L. Rivard, Edgewood, NM (US)

(*) Notice: Subject to any disclaimer, the term of this patent is extended or adjusted under 35 U.S.C. 154(b) by 1241 days.

(21) Appl. No.: 14/949,252

(22) Filed: Nov. 23, 2015

(65) Prior Publication Data

US 2016/0143368 A1     May 26, 2016

Related U.S. Application Data

(60) Provisional application No. 62/258,164, filed on Nov. 20, 2015, provisional application No. 62/083,802, filed on Nov. 24, 2014.

(51) Int. Cl.
*A61F 13/12* (2006.01)
*A61F 13/64* (2006.01)
*A61F 13/15* (2006.01)

(52) U.S. Cl.
CPC ............ *A61F 13/126* (2013.01); *A61F 13/64* (2013.01); *A61F 2013/15276* (2013.01)

(58) Field of Classification Search
CPC . A61F 13/126; A61F 13/64; A61F 2013/5276
See application file for complete search history.

(56) References Cited

U.S. PATENT DOCUMENTS

| | | | |
|---|---|---|---|
| 2,067,537 A * | 1/1937 | Kost | A44C 5/0046 223/109 R |
| 4,244,057 A * | 1/1981 | Burnham | A41D 19/0024 2/160 |
| 4,536,889 A * | 8/1985 | Taylor | A44C 5/0046 2/160 |
| 5,467,478 A | 11/1995 | Slaughter et al. | |
| 5,895,408 A * | 4/1999 | Pagan | A61B 17/24 604/1 |
| 6,270,510 B1 | 8/2001 | Westendorf | |
| 2007/0259025 A1* | 11/2007 | Strocel | A61K 31/045 424/443 |
| 2011/0088132 A1* | 4/2011 | McNamee-Sollars | A41D 27/12 2/46 |
| 2013/0219645 A1 | 8/2013 | Dowd | |
| 2017/0224539 A1* | 8/2017 | Hart | A61F 13/126 |

* cited by examiner

*Primary Examiner* — Tatyana Zalukaeva
*Assistant Examiner* — Gabriella E Burnette
(74) *Attorney, Agent, or Firm* — Kevin L. Soules; Loza & Loza, LLP

(57) ABSTRACT

A nose wiping device comprises a knobbed base structure, a cover enclosing the knobbed base structure, and connecting member attached to a first end of the cover and a second end of the cover. The nose wiping device is configured to be worn around a limb thereby allowing removal of nasal drip.

13 Claims, 4 Drawing Sheets

LIMB-MOUNTED NOSE WIPING DEVICE

CROSS REFERENCE TO RELATED APPLICATION

This patent application claims the priority and benefit under 35 U.S.C. § 119(e) of U.S. Provisional Patent Application Ser. No. 62/083,802 filed Nov. 24, 2014, entitled "LIMB-MOUNTED NOSE WIPING DEVICE." U.S. Provisional Patent Application Ser. No. 62/083,802 is herein incorporated by reference in its entirety. This patent application also claims the priority and benefit under 35 U.S.C. § 119(e) of U.S. Provisional Patent Application Ser. No. 62/258,164 filed Nov. 20, 2015, entitled "LIMB-MOUNTED NOSE WIPING DEVICE." Provisional Patent Application Ser. No. 62/258,164 is herein incorporated by reference in its entirety.

TECHNICAL FIELD

Embodiments are related to clothing and athletic gear. More particularly, embodiments are related to a wearable nose wiping device.

BACKGROUND

Persons engaged in activities, particularly in cold weather, or who suffer from seasonal allergies, frequently experience dripping nasal fluid, which can be uncomfortable, distracting, and unhygienic. Many activities may make the manipulation of a handkerchief or tissue, the reaching to grasp one from a pocket or bag, and its disposal after use, awkward, inconvenient, and potentially dangerous. For example, a bicyclist removing his/her hands from the handlebar of a bicycle for more than a brief moment is unsafe. A skier or hiker removing heavy gloves requires exposure to the external environment. A fisherman often uses both hands to cast or to reel in a catch prohibiting the fisherman from grabbing a tissue. Thus, it may be difficult to manipulate a handkerchief or tissue when the available time to wipe the nose is limited, or mobility of the person's digits are limited (as when wearing heavy gloves or mittens) or is impaired by amputation or other disability.

Also, a handkerchief or tissue may not absorb dripping nasal fluid until it exits the nasal cavity. Thus, a person may have to wait until fluid has dripped down over the upper lip, or use fingers or knuckles to insert the handkerchief or tissue slightly into the nasal cavity to prevent dripping. This exposes the person's hands or fingers to nasal fluid at a time when it is impossible or inconvenient to wash the hands before touching food or other surfaces.

Accordingly, there is a need for improved systems, methods, and apparatuses hands free removal of nasal drip.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

The embodiments disclosed herein provide an effective hands free nasal drip wiping device by providing an absorbent pad fashioned with ridges or bumps and/or a napped material. The pad includes slight protrusions configured to fit gently into the interior of the nostril so as to capture excess fluid before it exits the nose. The nasal drip wiping device can be permanently attached to an elastic or adjustable strap that can be worn on one of the user's limbs, most frequently on the wrist, either inside or outside clothing.

The embodiments disclosed herein address hygienic concerns because the fingers and hands do not touch the nasal fluid or the moistened absorbent material, so that the user does not transfer nasal fluid to food or other surfaces while engaged in an activity.

It is therefore an aspect of the disclosed embodiments to provide a system, method and apparatus for removing nasal drip. For example, in an embodiment a nose wiping apparatus comprises a knobbed base structure, a cover enclosing the knobbed base structure, and connecting member attached to a first end of the cover and a second end of the cover.

In an embodiment, the connecting member comprises an elastic strap wherein an elasticity of the elastic strap engages the elastic strap to a limb. In another embodiment the connecting member comprises a first connecting member attached the first end of the cover; a second connecting member attached to the second end of the cover; and a fastener for attaching the first connecting member to the second connecting member. The fastener comprises at least one of a hook and loop fastener, a buckle, a hook and eye fastener, a lace and lace hole arrangement, at least one snap and at least one snap receptacle, and at least one button and at least one button hole.

In another embodiment the cover comprises at least one of a fabric, a pad, and a permeable membrane. The fabric comprises at least one of a napped fabric, a breathable fabric, a wicking fabric, and an anti-microbial fabric.

In another embodiment the knobbed base structure further comprises a base support and at least one knob attached to the base support. Each of the at least one knobs further comprises at least two laterally offset knobs and at least two raised struts wherein an intersection of the raised struts forms the knob. In another embodiment the knobbed base structure further comprises a solid surface plane, and at least one dimple formed in the solid surface plane. The nose wiping apparatus is configured to be worn around a limb thereby allowing removal of nasal drip.

BRIEF DESCRIPTION OF THE DRAWINGS

The accompanying figures, in which like reference numerals refer to identical or functionally similar elements throughout the separate views and are incorporated in and form a part of the specification, further illustrate aspects of the embodiments and, together with the background, brief summary, and detailed description, serve to explain the principles of the embodiments.

DETAILED DESCRIPTION

Figure 1:
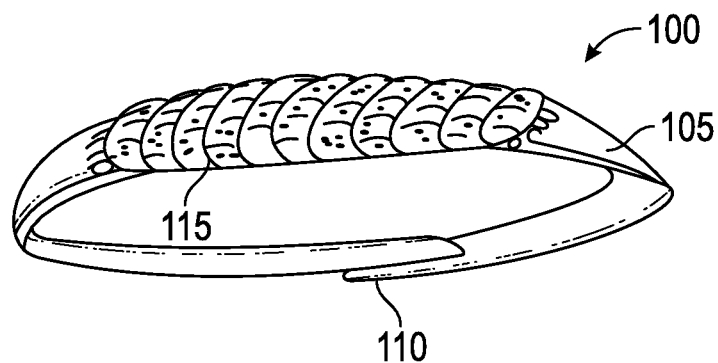
FIG. 1 illustrates a nose wiping apparatus in accordance with an example embodiment.

The following description contains a series of exemplary embodiments of systems, methods and apparatuses for removing nasal drip not previously known.

The exemplary embodiments described more fully hereinafter make reference to the accompanying drawings, in which illustrative embodiments are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The particular values and configurations discussed in the following non-limiting examples can be varied and are cited merely to illustrate one or more embodiments and are not intended to limit the scope thereof.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence, or addition, of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. In addition, the term "based on" may be understood as not necessarily intended to convey an exclusive set of factors and may, instead, allow for existence of additional factors not necessarily expressly described, again, depending at least in part on context.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Everyone has experienced a situation where it is either inconvenient or impossible to wipe the nasal drip from one's nose. This is especially true for people participating in outdoor activities, particularly when the ambient temperature is cold. The present embodiments provide a limb mounted nose wiping device that comprises a base structure covered by an absorbent pad fashioned with ridges or bumps and/or a napped material capable of protruding slightly into the interior of the user's nostril so as to capture excess fluid before it exits the nose. The absorbent pad can be permanently or temporarily attached to an adjustable strap that can be worn on one of the user's limbs, most frequently on the wrist, either inside or outside user's clothing. The adjustable and/or elastic strap ensures that the limb-mounted nose wiping device is securely fixed around the user's limb. The limb-mounted nose wiping device can be removed and laundered after use.

The limb mounted nose wiping device described herein prevents the user's fingers and/or hands from touching the nasal fluid or the moistened absorbent material, so that the user does not transfer nasal fluid to food or other surfaces.

FIG. 1 illustrates a limb-mounted nose wiping device 100 in accordance with embodiments of the present invention. The limb-mounted nose wiping device 100 generally includes a cover 115 enclosing a knobbed base structure. The cover 115 is attached to a connecting member 105, and a fastener 110.

In one embodiment the cover 115 may include be sewn or otherwise attached to and/or around the base structure and permanently connected to the connecting member 105. In other embodiments, the cover 115 may be removable from one or both of the base structure and connecting member 105 via a hook and loop connection or other such means. The cover 115 and the entire limb-mounted nose wiping device 100 are washable and may be sanitized by washing either by hand or using a conventional washing machine.

Figure 2:
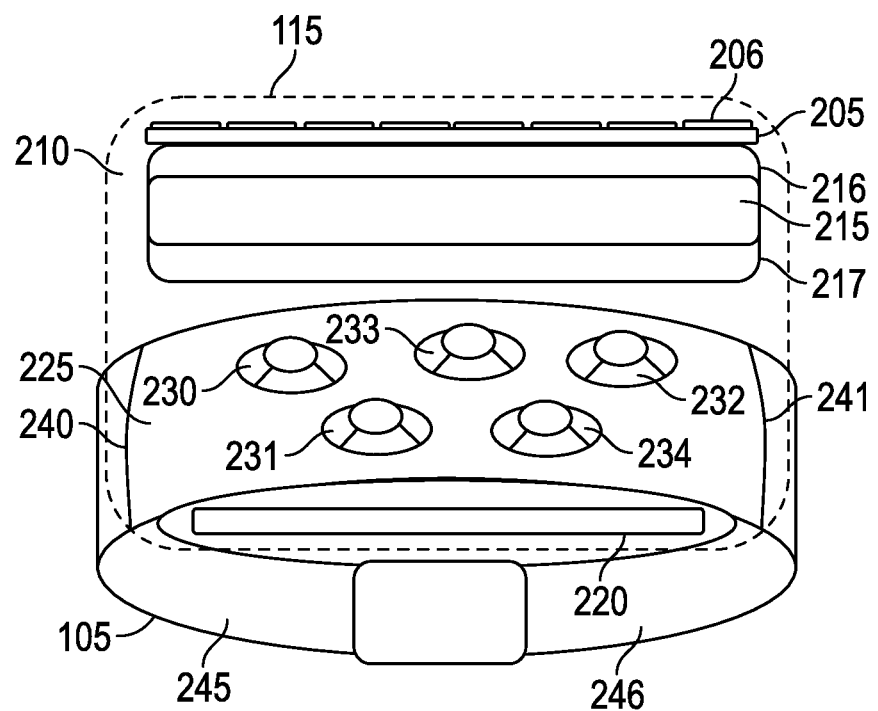
FIG. 2 illustrates a layered view of a nose wiping apparatus in accordance with an another example embodiment.

The cover 115 may be formed as a number of layers of material as illustrated in FIG. 2. In one embodiment the cover 115 has an outer fabric 205 that is exposed on the top side of the limb-mounted nose wiping device 100, that is intended to contact the nose. The outer fabric layer 205 can be a technical fabric with wicking and/or anti-microbial properties. The outer fabric 205 may be napped 206 (and as shown in FIG. 1) and stretchable. The outer fabric layer 205 can also be knit and/or woven.

The cover 115 may include a second layer 210 below the outer fabric 205 but above the base structure 225 that serves as padding. In one embodiment the second layer 210 can be a permeable membrane configured to absorb nasal fluid that is collected during use. In one embodiment the permeable membrane comprises an absorbent pad 215 formed between two sheets of material. The absorbent pad 215 absorbs nasal fluids. The absorbent pad can be attached to a permeable top sheet 216 and impermeable bottom sheet 217 that are sealed together into second layer 210. The constituent materials in second layer 210 may be antimicrobial. It should be appreciated that the second layer 210 may be used with or without outer fabric 205. In other embodiments the second layer 210 can simply be a pad configured to soften the contact between the base structure and user's nose.

The cover 115 can have an inner fabric 220 formed under or otherwise below the base structure 225. The inner fabric 220 is the layer in contact with the user's wrist or limb. The inner fabric 220 can be a technical breathable fabric that allows for evaporation of sweat from the skin. The breathable characteristics of inner fabric 220 are useful in warm weather as well as cold, when sweat may be prevalent on a user's limb. In other embodiments connecting member 105, which is also in contact with a user's skin, may be formed of the same technical breathable fabric used as inner fabric 220.

Figure 3:
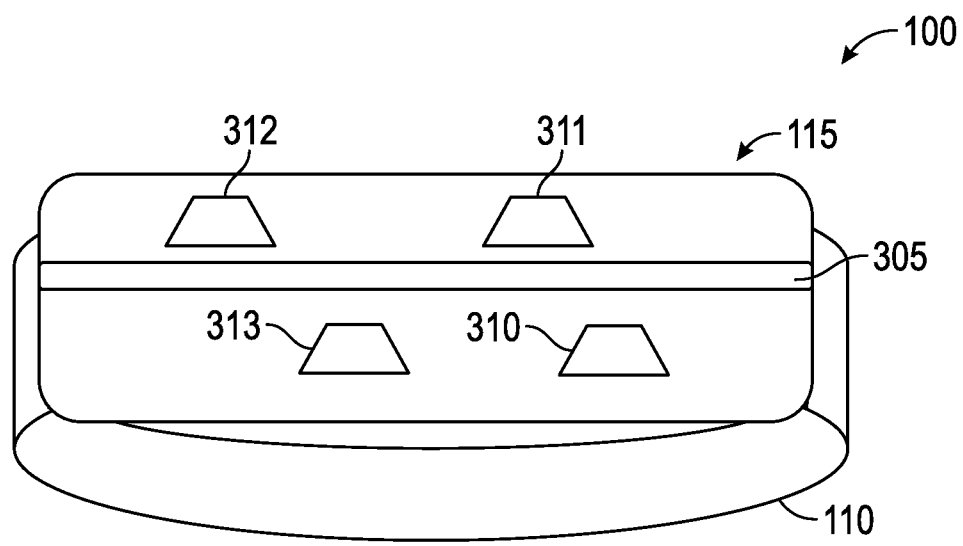
FIG. 3 illustrates a nose wiping apparatus in accordance with an example embodiment.
Figure 4:
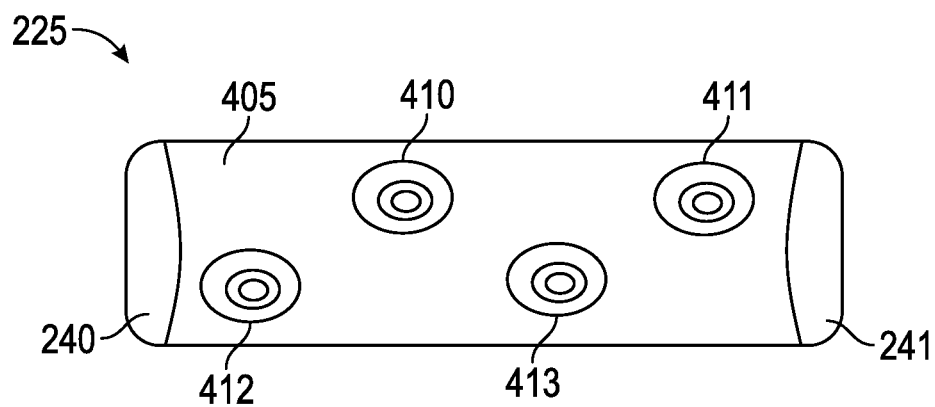
FIG. 4 illustrates a support structure in accordance with an example embodiment.

FIG. 3 illustrates another embodiment where the cover 115 may be formed to intrinsically provide small bumps 310, 311, 312, and 313 or ridges that protrude slightly into the nose. The shape can be achieved by sewing the cover material into such bumps or ridges.

FIG. 3 also illustrates joint 305, which can be formed in cover 115 in order to allow cover 115 to be removed from base structure 225. Joint 305 provides an opening in the cover 115 for insertion and removal of the inner contents such as the base structure 205, second layer 210, etc. Joint 305 can be formed as a hook and loop joint, buttons and button holes, snaps and snap receptacles, laces and lace holes, or a hook and eye style joint. Joint 305 illustrated in FIG. 3 is exemplary. Joint 305 can be located at the outer surface of cover 115 (away from the limb) as shown in FIG. 3, on the inner surface of cover 115 (next to the wrist), on the inner fabric 220, and/or on any of the 4 edges of the cover 115.

A base structure, frame, and/or skeleton 225, may be inserted between the outer fabric 205 and/or second layer 210 of cover 115, and the inner fabric 220. FIG. 2 is intended to illustrate the various layers of cover 115, and their general arrangement around base structure 225. However, it should be appreciated that the various layers of cover 115 can be permanently fixed around, and entirely enclose base structure as a sleeve or other such arrangement.

As illustrated in FIG. 2, base structure 225 can comprise a plurality of knobs such as knobs 230, 231, 232, 233, and 234. Any number of such knobs may be used and the knobs illustrated in FIG. 2 are exemplary and not intended to limit the number of knobs that can be used. Knobs 230, 231, 232, 233, and 234 can be any size but are preferably raised 1 cm-1.5 cm above the base structure 225, in order to comfortably engage the inside of a nostril. Base structure 225 may be any size but is preferably between 2.5 in and 3 in in length. Base structure 225 also includes bending 240 and 241 at the two ends of the frame. Bent sections 240 and 241 of base structure 225 resemble a cuff bracelet, that conforms to the natural shape of a limb. This is intended to hold the base structure, and by extension the entire limb-mounted nose wiping device 100 more securely on the wrist or limb. The base structure can be flexible.

FIGS. 4 and 5A-5C provide illustrations of embodiments of base structure 225. In FIG. 4A base structure 225 is illustrated as a solid surface plane 405, with dimples 410, 411, 412, and 413. The dimples can be constructed of polymer or other such material that is semi-gelatinous and/or semi-rigid. The solid surface plane 405 can includes bends 240 and 241 to ensure the base structure 225 fits snugly around the user's limb. The solid surface plane 405 can be formed of flexible plastic, or other similar flexible material, so that it is capable of bending and conforming generally to the contour of the user's limb, while remaining stiff enough to maintain some shape during use. The flexible material can be sufficiently durable to withstand basic and common impacts likely to be encountered during athletic and/or other outdoor activities.

Figure 5A:
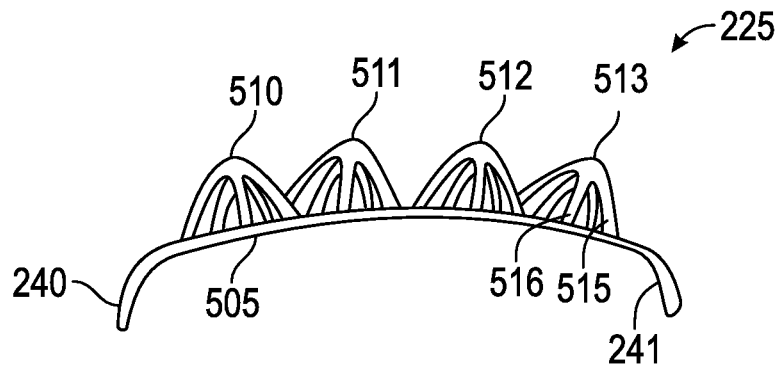
FIG. 5A illustrates a side view of a support structure in accordance with an example embodiment.

FIG. 5A illustrates a side elevation view of another embodiment of base structure 225. In this embodiment, base structure 225 includes a base support 505, with knobs 510, 511, 512, and 513 protruding there from and anchored thereto. Each of knobs 510, 511, 512, and 513 is formed from at least two struts, for example struts 515 and 516 shown for knob 513. Additional struts, such as struts 530 and 531, may be included in each of knobs 510, 511, 512, and 513 as necessary for increased rigidity. The struts are fixedly connected to base support 505 and are molded or otherwise formed into protrusions. Base support 505 includes bent sections 240 and 241 which ensure a comfortable rigid engagement with the user's limb.

Figure 5B:
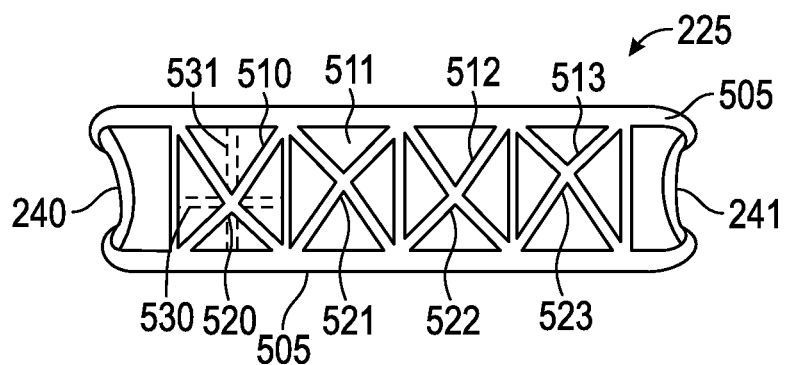
FIG. 5B illustrates a top view of a support structure and struts in accordance with an example embodiment.
Figure 5C:
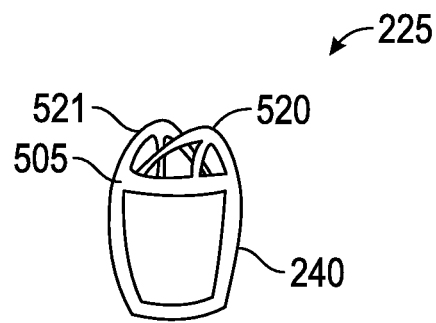
FIG. 5C illustrates an elevation view of a support structure and struts in accordance with an example embodiment.

FIG. 5B illustrates a top view of base structure 225. Of particular note in this view is the arrangement of the knob tips. Specifically, knob 510 has an associated knob tip 520, where the struts forming knob 510 reach their apex. Similarly, knob 511 has knob tip 521, knob 512 has knob tip 522, and knob 513 has knob 523. Each of the knob tips 520, 521, 522, and 523 are formed by the respective struts, such that the knob tips do not laterally align. Instead, the alignment of knob tips 520, 521, 522, and 523 is laterally staggered. This staggered arrangement facilitates the insertion of the knob tip into a nostril. It should be appreciated that other arrangements of knob tips 520, 521, 522, and 523 may also be used and may include differing numbers of knobs and knob tips depending on design considerations. FIG. 5C illustrates the staggered lateral alignment of knob tips 520 and 521 when viewed from an end elevation perspective.

Connecting member 105 is illustrated in FIG. 2. In one embodiment connecting member 105 can includes at least two straps 245 and 246, or other such connecting devices. Each of straps 245 and 246 can be sewn or otherwise connected to the ends of cover 115. Straps 245 and 246 are joined via fastener 110. Fastener 110 may be styled as a buckle and buckle holes, hook and eye, lace and lace holes, hook and loop, buttons and button holes, or snaps and snap receptacles. In other embodiment fastener 110 may be a buckle of any kind, including but not limited to a strap 245 threading through two parallel slots and/or two adjacent rings affixed to strap 246; a military style buckle where a hinged clamp on strap 246 closes on to the strap 245, and teeth in the clamp hold the strap 245 secure; and/or strap 245 attached to a male or female connector that mates with a male or female connector attached to strap 246.

In another embodiment, connecting member 105 can be a single piece having the ends permanently sewn or otherwise removably connected to cover 115, with the entire connecting member 105 being elastic, or other such stretchable material, such that it can expand over the hand and is then held in place by the elasticity of the connecting member 105. Such an embodiment of connecting member 105 is illustrated in FIG. 3.

Figure 6:
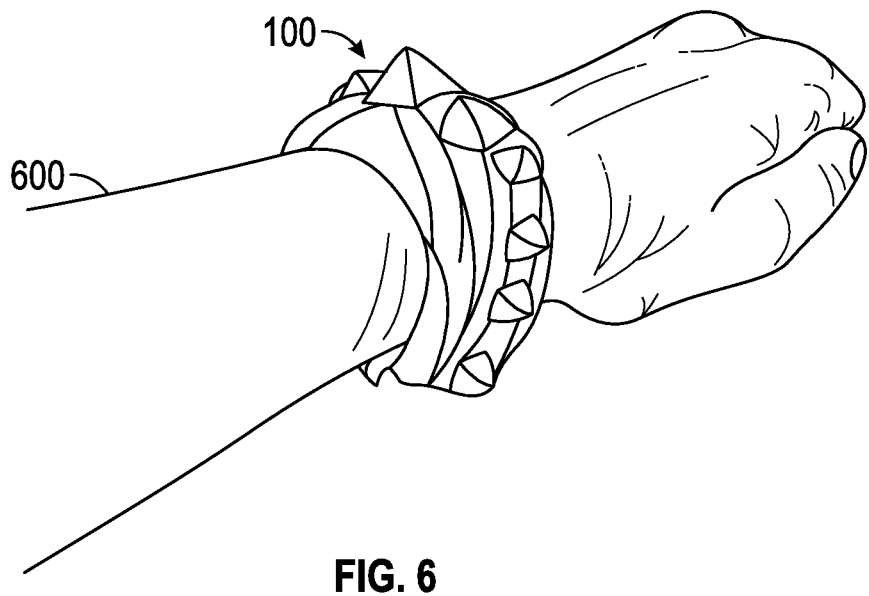
FIG. 6 illustrates a nose wiping apparatus engaged to a user's limb in accordance with an example embodiment.

FIG. 6 illustrates a limb mounted nose wiping device attached to the limb 600 of a user. It should be appreciated that in most circumstances limb 600 will be an arm or wrist. However, the limb mounted nose wiping device may be used with other limbs, including legs, ankles, or prosthetic attachments, without departing from the scope of the invention. Limb mounted nose wiping device 100 could be used during any sporting, athletic, outdoor, recreational, or work related activity including but not limited to cycling, running, fishing, skiing, or other such activities in which the user's hands are engaged but it would be desirable to be able to wipe his/her nose with as minimal a disruption of the activity as possible. The limb mounted nose wiping device 100 may also be useful for those who suffer from seasonal allergies or other such ailments and do not have ready access to nose tissue.

Figure 7:
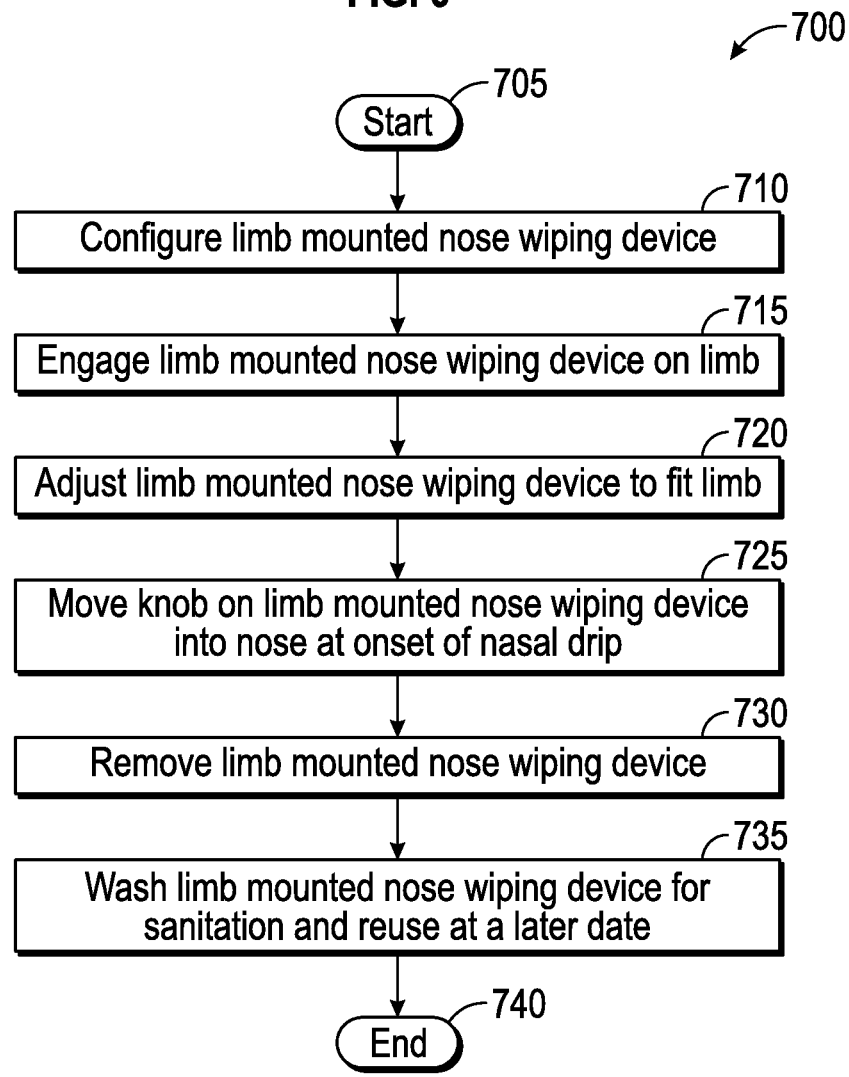
FIG. 7 illustrates a flow chart of steps associated with the use of a nose wiping device in accordance with an example embodiment.

FIG. 7 illustrates steps associated with a method 700 for removing nasal fluid using a limb mounted nose wiping device in accordance with an embodiment of the invention. The method begins at step 705. A step 710 a limb mounted nose wiping device such as limb mounted nose wiping device 100 can be configured to include a base structure covered by a covering, and a connecting member as described herein.

As shown at step 715, the limb mounted nose wiping device can next be engaged on the user's limb. As discussed above, the limb may be an arm, wrist, leg, or prosthetic limb. Next at step 720 the limb mounted nose wiping device can be adjusted via fasteners, or the elastic tension in the connecting member to fit snugly on the user's limb with the covered knobs positioned to conveniently reach the user's nose.

Once the limb mounted nose wiping device is in place the user may begin to participate in an activity. At the first sign of nasal drip the user can insert or otherwise rub the covered knobs in or on the user's nasal cavity to collect the nasal drip before it is exposed as shown at 725. Nasal drips which have already exited the nasal cavity may also be removed.

Once the user has completed the activity, the limb-mounted nose wiping device can be removed as illustrated at 730. At this point, the limb-mounted nose wiping device can be washed as shown at 735 in a washing machine or in another suitable manner, to sanitize the limb-mounted nose wiping device before its reuse. The method ends at 740.

Based on the foregoing, it can be appreciated that a number of embodiments, preferred and alternative, are disclosed herein. For example, in an embodiment a nose wiping apparatus comprises a knobbed base structure, a cover enclosing the knobbed base structure, and connecting member attached to a first end of the cover and a second end of the cover.

In one embodiment the connecting member further comprises an elastic strap wherein an elasticity of the elastic strap engages the elastic strap to a limb.

In another embodiment the connecting member comprises a first connecting member attached the first end of the cover; a second connecting member attached to the second end of the cover; and a fastener for attaching the first connecting member to the second connecting member. The fastener comprises at least one of a hook and loop fastener, a buckle, a hook and eye fastener, a lace and lace hole arrangement, at least one snap and at least one snap receptacle, and at least one button and at least one button hole.

In another embodiment the cover comprises at least one of a fabric, a pad, and a permeable membrane. The fabric comprises at least one of a napped fabric, a breathable fabric, a wicking fabric, and an anti-microbial fabric.

In one embodiment the knobbed base structure further comprises a base support and at least one knob attached to the base support. Each of the at least one knobs further comprises at least two laterally offset knobs and at least two raised struts wherein an intersection of the raised struts forms the knob.

In another embodiment the knobbed base structure further comprises a solid surface plane, and at least one dimple formed in the solid surface plane.

In an embodiment the nose wiping apparatus is configured to be worn around a limb thereby allowing removal of nasal drip.

In another embodiment a nose wiping system comprises a knobbed base structure comprising a base support and at least one knob attached to the base support wherein at least two raised intersecting struts form the knob, a cover enclosing the knobbed base structure wherein the cover comprises at least one of fabric, a pad, and a permeable membrane, and a connecting member attached to a first end of the cover and a second end of the cover wherein the nose wiping apparatus is configured to be worn around a limb thereby allowing for removal of nasal drip.

In an embodiment of the system the connecting member further comprises an elastic strap wherein an elasticity of the elastic strap engages the elastic strap to a limb.

In another embodiment of the system the connecting member further comprises a first connecting member attached the first end of the cover, a second connecting member attached to the second end of the cover, and a fastener for attaching the first connecting member to the second connecting member. The fastener comprises at least one of a hook and loop fastener, a buckle, a hook and eye fastener, a lace and lace hole arrangement, at least one snap and at least one snap receptacle, and at least one button and at least one button hole.

In another embodiment a method for removing nasal drip comprises affixing a nose wiping device to a limb wherein the nose wiping device comprises a knobbed base structure, a cover enclosing the knobbed base structure, and a connecting member attached to a first end of the cover and a second end of the cover; applying the nose wiping device to a nostril at an onset of nasal drip; collecting the nasal drip with the nose wiping device. The method further comprises removing the nose wiping device from the limb, and sanitizing the nose wiping device. Sanitizing the nose wiping device comprises washing the nose wiping device.

In another embodiment affixing the nose wiping device to a limb comprises: engaging the connecting member to the limb with an elastic strap connected to the cover.

In another embodiment affixing the nose wiping device to a limb comprises engaging the connecting member to the limb wherein the connecting member comprises a first connecting member attached the first end of the cover, a second connecting member attached to the second end of the cover, and a fastener for attaching the first connecting member to the second connecting member.

In another embodiment applying the nose wiping device to a nostril at the onset of nasal drip further comprises inserting a knob associated with the knobbed base structure into the nostril.

It will be appreciated that variations of the above-disclosed and other features and functions, or alternatives thereof, may be desirably combined into many other different systems or applications. Also, it will be appreciated that various presently unforeseen or unanticipated alternatives, modifications, variations or improvements therein may be subsequently made by those skilled in the art which are also intended to be encompassed by the following claims.

What is claimed is:

1. A method for removing nasal drip comprising:
affixing a nose wiping device to a limb wherein said nose wiping device comprises a base structure with a plurality of knobs formed thereon, said plurality of knobs being laterally offset, wherein each of said plurality of knobs comprises at least two intersecting raised struts, a cover enclosing said base structure, and a connecting member attached to said cover;

applying said nose wiping device to a nostril at an onset of nasal drip;

collecting said nasal drip with said nose wiping device.

2. The method of claim 1 further comprising:
removing said nose wiping device from said limb; and
sanitizing said nose wiping device.

3. The method of claim 2 wherein sanitizing said nose wiping device comprises washing said nose wiping device.

4. The method of claim 1 wherein affixing said nose wiping device to a limb comprises:
engaging said connecting member to said limb with an elastic strap connected to said cover.

5. The method of claim 1 wherein affixing said nose wiping device to a limb comprises:
engaging said connecting member to said limb wherein said connecting member comprises a first connecting strap attached to said cover, a second connecting strap attached to said cover, and a fastener for attaching said first connecting strap to said second connecting strap.

6. The method of claim 1 wherein applying said nose wiping device to a nostril at the onset of nasal drip further comprises inserting a knob associated with said base structure into said nostril.

7. A nose wiping system comprising:
a base structure comprising a base support and at least one knob attached to said base support wherein at least two raised intersecting struts form said knob;
a cover enclosing said base structure; and
a connecting member attached to said cover.

8. The nose wiping system of claim 7 wherein said connecting member is elastic.

9. The nose wiping system of claim 7 wherein said connecting member further comprises:
a first connecting strap attached to said cover;
a second connecting strap attached to said cover; and
a fastener for attaching said first connecting strap to said second connecting strap.

10. The system of claim 7 wherein said fastener comprises at least one of:
a hook and loop fastener;
a buckle;
a hook and eye fastener;
a lace and lace hole arrangement;
at least one snap and at least one snap receptacle; and
at least one button and at least one button hole.

11. The system of claim 7 wherein said cover comprises at least one of:
a fabric;
a second layer configured to provide padding; and
a permeable membrane.

12. The cover of claim 11 wherein said fabric comprises at least one of:
a napped fabric;
a breathable fabric;
a wicking fabric; and
an anti-microbial fabric.

13. The nose wiping system of claim 7 wherein said nose wiping system is configured to be worn around a limb thereby allowing removal of nasal drip.

* * * * *